(12) United States Patent
Fang et al.

(10) Patent No.: US 11,564,575 B2
(45) Date of Patent: Jan. 31, 2023

(54) MAGNETIC RESONANCE-POSITRON EMISSION TOMOGRAPHY IMAGING APPARATUS

(71) Applicant: SHANGHAI UNITED IMAGING HEALTHCARE CO., LTD., Shanghai (CN)

(72) Inventors: Fuyi Fang, Shanghai (CN); Lingzhi Hu, Houston, TX (US); Qiang He, Shanghai (CN); Wei Luo, Shanghai (CN); Feng Xu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 441 days.

(21) Appl. No.: 16/251,013

(22) Filed: Jan. 17, 2019

(65) Prior Publication Data
US 2019/0239747 A1   Aug. 8, 2019

(30) Foreign Application Priority Data

Jan. 17, 2018  (CN) .......................... 201810045327.9
Dec. 30, 2018  (CN) .......................... 201822259323.9

(51) Int. Cl.
*A61B 5/055* (2006.01)
*A61B 5/00* (2006.01)
(Continued)

(52) U.S. Cl.
CPC ............ *A61B 5/0035* (2013.01); *A61B 5/055* (2013.01); *A61B 6/037* (2013.01); *A61B 6/4411* (2013.01);
(Continued)

(58) Field of Classification Search
CPC ....... A61B 5/0035; A61B 5/055; A61B 6/037; G01R 33/481
See application file for complete search history.

(56) References Cited

U.S. PATENT DOCUMENTS

2005/0107681 A1   5/2005  Griffiths
2006/0251312 A1   11/2006 Krieg et al.
(Continued)

FOREIGN PATENT DOCUMENTS

CN   101740862 A   6/2010
CN   101856229 A   10/2010
(Continued)

OTHER PUBLICATIONS

First Office Action in Chinese Application No. 201810045327.9 dated Sep. 27, 2020, 24 pages.
(Continued)

*Primary Examiner* — Bill Thomson
*Assistant Examiner* — Aminah Asghar
(74) *Attorney, Agent, or Firm* — Metis IP LLC

(57) ABSTRACT

An MR-PET apparatus is provided. The MR-PET apparatus may include a supporting component, a PET detection device, an RF coil, and a signal shielding component. The PET detection device may be supported on the supporting component. The PET detection device may be configured to receive a plurality of photons. The RF coil may be configured to generate or receive a radio frequency (RF) signal. The signal shielding component may be placed between the PET detection device and the RF coil. The signal shielding component may be configured to shield the PET detection device from at least part of the RF signal.

17 Claims, 11 Drawing Sheets

(51) Int. Cl.
*A61B 6/00* (2006.01)
*A61B 6/03* (2006.01)
(52) U.S. Cl.
CPC ...... *A61B 6/4417* (2013.01); *A61B 2562/182* (2013.01)

(56) References Cited

U.S. PATENT DOCUMENTS

| | | | |
|---|---|---|---|
| 2007/0055127 A1 | 3/2007 | Ladebeck et al. | |
| 2008/0068017 A1* | 3/2008 | Eberler | G01T 1/1603 324/318 |
| 2009/0051362 A1* | 2/2009 | Nistler | G01R 33/34046 324/318 |
| 2009/0146066 A1 | 6/2009 | Renz et al. | |
| 2009/0206836 A1* | 8/2009 | Eberler | A61B 5/055 324/307 |
| 2010/0219347 A1 | 9/2010 | Schulz et al. | |
| 2012/0022364 A1* | 1/2012 | Caruba | A61B 6/037 600/425 |
| 2013/0193974 A1* | 8/2013 | McBroom | G01R 33/34 324/322 |
| 2013/0234710 A1 | 9/2013 | Kanno et al. | |
| 2013/0284936 A1* | 10/2013 | McBroom | G01R 33/481 250/363.03 |
| 2014/0021953 A1 | 1/2014 | Corbeil et al. | |
| 2014/0253122 A1* | 9/2014 | Leussler | G01R 33/4215 324/309 |
| 2015/0002150 A1* | 1/2015 | Weissler | A61B 6/4417 324/309 |
| 2015/0362568 A1 | 12/2015 | Lips | |
| 2016/0103194 A1* | 4/2016 | Schulz | G01R 33/56518 324/309 |
| 2018/0028092 A1* | 2/2018 | Okamoto | A61B 6/4417 |

FOREIGN PATENT DOCUMENTS

| | | |
|---|---|---|
| CN | 205181369 U | 4/2016 |
| WO | 2015018894 A1 | 2/2015 |

OTHER PUBLICATIONS

The Second Office Action in Chinese Application No. 201810045327.9 dated Apr. 27, 2021, 27 pages.
The Third Office Action in Chinese Application No. 201810045327.9 dated Jul. 21, 2021, 29 pages.

* cited by examiner

MAGNETIC RESONANCE-POSITRON EMISSION TOMOGRAPHY IMAGING APPARATUS

CROSS-REFERENCE TO RELATED APPLICATIONS

This application claims priority to Chinese Patent Application No. 201810045327.9 filed on Jan. 17, 2018, and Chinese Patent Application No. 201822259323.9 filed on Dec. 30, 2018, the entire contents of each of which are hereby incorporated by reference.

TECHNICAL FIELD

This present disclosure relates to an imaging apparatus, and more particularly, relates to a magnetic resonance (MR)-positron emission tomography (PET) imaging apparatus.

BACKGROUND

Magnetic resonance (MR)-positron emission tomography (PET) is a hybrid imaging technique that incorporates both MR (e.g., a soft tissue morphological imaging technique) and PET (e.g., a functional imaging technique). In a conventional MR-PET imaging apparatus, components of a PET imaging apparatus (e.g., one or more PET detection devices) and components of an MR imaging apparatus (e.g., an RF coil, a main magnet, a gradient magnet) may be integrated. For example, a PET detection device may be mounted on a supporting component (e.g., a cylindrical supporting component), and placed between an RF coil and a gradient magnet of the MR system.

In order to ensure that the PET detection device is stably mounted and remains relatively static during use, the supporting component in the conventional MR-PET imaging apparatus may be made of a material with high strength. However, materials with high strength usually have a high attenuation rate of gamma rays (e.g., the particles detected by the PET detection devices) and significantly reduce the accuracy of image data generated by the PET detection devices. Furthermore, as the RF coil and the PET detection devices in the MR-PET imaging apparatus often work simultaneously, the inference or coupling between the RF coil and the PET detection device may occur and reduce the performance of either or both of the RF coil and the PET detection device.

Therefore, it is desirable to provide an MR-PET imaging apparatus that may stably hold the PET detection device without significantly reducing the accuracy of signals detected by the PET detection devices and also reduce or eliminate the inference or coupling between an RF coil and the PET detection device.

SUMMARY

According to an aspect of the present disclosure, an MR-PET apparatus is provided. The MR-PET apparatus may include a supporting component, a PET detection device, an RF coil, and a signal shielding component. The PET detection device may be supported on the supporting component. The PET detection device may be configured to receive a plurality of photons. The RF coil may be configured to generate or receive a radio frequency (RF) signal. The signal shielding component may be placed between the PET detection device and the RF coil. The signal shielding component may be configured to shield the PET detection device from at least part of the RF signal.

In some embodiments, the supporting component may include a first section and a second section. The second section may have a lower attenuation rate of the photons than the first section. The PET detection device may be positioned such that at least a portion of the plurality of photons penetrate through the second section and reach the detection device.

In some embodiments, the supporting component including the first section and the second section may be an integral body. The second section may be thinner than the first section.

In some embodiments, the first section and the second section may be made of carbon fiber or glass fiber.

In some embodiments, the supporting component may further include an auxiliary supporting body mechanically attached to the second section.

In some embodiments, the auxiliary supporting body may be made of a foam material or a honeycomb material.

In some embodiments, the auxiliary supporting body may have a lower attenuation rate of photons than the first section and the second section.

In some embodiments, the signal shielding component may be made of one or more electrically conductive materials.

In some embodiments, the signal shielding component may include a shielding layer mechanically attached to at least part of an external surface of the PET detection device.

In some embodiments, the signal shielding component may include a shielding layer having a first side and a second side. The first side of the shielding layer may be mechanically attached to the RF coil and the second side of the shielding layer may be mechanically attached to the PET detection device.

In some embodiments, the RF coil may include a first count of coil units. The PET detection device may include a second count of detection units. The first count may be the same as the second count.

In some embodiments, the signal shielding component may include a third count of shielding units. The third count may be the same as the first count or the second count. Each of the coil units may be paired with one of the shielding units. Each pair of a coil unit and a shielding unit may be installed on a connection board unit. Each connection board unit may be mechanically attached to one of the detection unit.

In some embodiments, the signal shielding component may include a shielding layer having a first side and a second side. The first side of the shielding layer may be mechanically attached to the RF coil. The second side of the shielding layer may be mechanically attached to the supporting component.

In some embodiments, the MR-PET apparatus may include an electrical insulation component placed between the RF coil and the signal shielding component. The electrical insulation component may be configured to electrically insulate the RF coil from the signal shielding component.

In some embodiments, at least one of the signal shielding component, the RF coil, or an electrical insulation component may be integrated on a same circuit board.

In some embodiments, the PET detection device may include a plurality of detection units. The plurality of detection units may be arranged in a ring shape.

In some embodiments, the RF coil may include at least one of a dipole coil, a birdcage coil, a transverse electromagnetic coil, a loop coil, or a surface coil.

In some embodiments, the signal shielding component may have a configuration of a film or a mesh.

In some embodiments, the MR-PET apparatus may include a gantry. The gantry may be configured to hold at least one of the supporting component, the PET detection device, the RF coil, or the signal shielding component. An inner surface of the gantry may form a detection region. The detection region may be configured to accommodate an object.

In some embodiments, the MR-PET apparatus may further include a main magnet configured to generate a main magnetic field, and a gradient magnet configured to generate magnetic field gradients.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
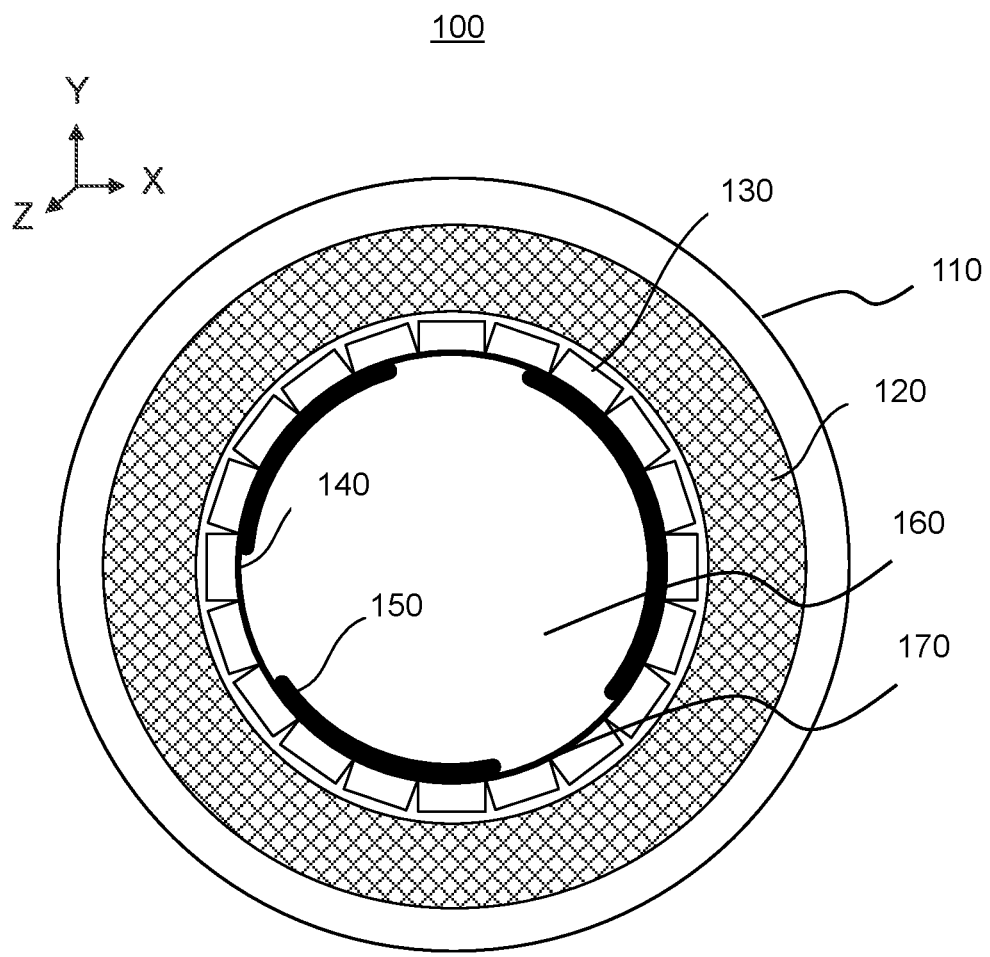
FIG. 1 is a cross-sectional view of an exemplary MR-PET apparatus according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/ units/blocks or divided into sub-modules/sub-units/sub-blocks despite their physical organization or storage. The description may be applicable to a system, an engine, or a portion thereof.

It will be understood that the terms "layer," "surface," "groove," "ring," etc. when used in this disclosure, refer to one or more parts with one or more specific purposes. However, a structure that may perform a same or similar function compared to a part exemplified above or referred to elsewhere in the present disclosure may be named differently from the present disclosure.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

It will be understood that an "inner surface" may refer to a surface that is close to or faces a scanned object and an "outer surface" may refer to a surface that is away from or opposite to a scanned object. An "external surface" may refer to a surface that is exposed to air or contact surfaces of another component and an "internal surface" may refer to a surface that is not exposed to air or invisible from the outside.

Spatial and functional relationships between elements (for example, between layers) are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

It should also be understood that terms such as "top," "bottom," "upper," "lower," "vertical," "lateral" "above," "below," "upward(s)," "downward(s)," "left-hand side" "right-hand side" "horizontal," and other such spatial reference terms are used in a relative sense to describe the positions or orientations of certain surfaces/parts/components of the MR-PET apparatus in relationship to other such features of the MR-PET apparatus when the MR-PET apparatus is in a normal operating position and may change if the position or orientation of the MR-PET apparatus changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

An aspect of the present disclosure relates to an MR-PET apparatus. The MR-PET apparatus may include a supporting component, a PET detection device, an RF coil, a signal shielding component, or the like. The signal shielding component may be an integral body that includes a first section and a second section. The first section and the second section may be made of a same material. The second section may include a groove. The thickness of the second section may be less than the thickness of the first section so that the second section may have a lower attenuation rate of photon rays than the first section. Photons generated by an object may penetrate through the second section and impinge on the PET detection device. The RF coil may generate a radio frequency (RF) signal to the object. The signal shielding component may be placed between the RF coil and the PET detection device. The signal shielding component may shield the PET detection device from at least part of the RF signal generated by the RF coil so as to reduce, e.g., inference or coupling between the PET detection device and the RF coil.

Figure 2:
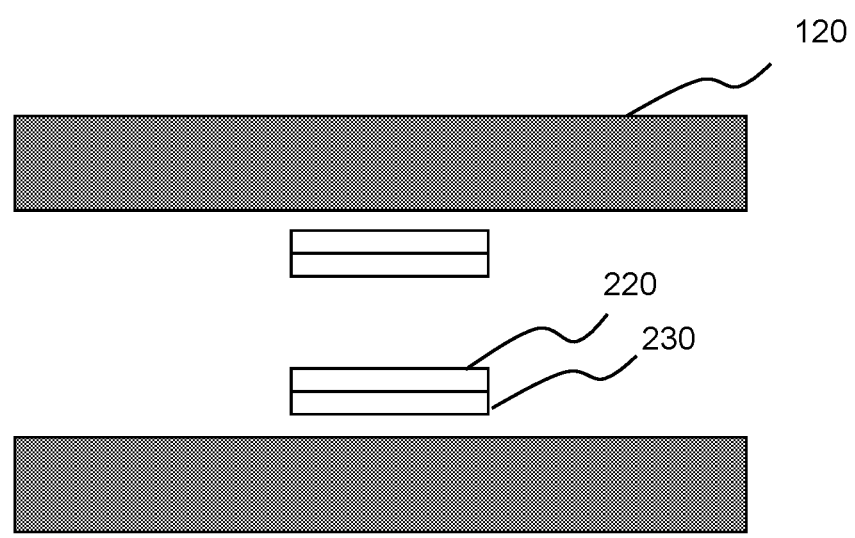
FIG. 2 is an axial sectional view of an exemplary MR-PET apparatus according to some embodiments of the present disclosure.

FIG. 1 is a cross-sectional view of an exemplary MR-PET apparatus according to some embodiments of the present disclosure. FIG. 2 is an axial sectional view of an exemplary MR-PET apparatus according to some embodiments of the present disclosure. In some embodiments, the MR-PET apparatus 100 may be an apparatus for generating an MR image and/or a PET image of an object. The MR image and/or the PET image may be generated individually or concurrently. The object may include a biological object and/or a non-biological object. The biological object may include a human being, an animal, a plant, or a portion thereof (e.g., a cell, a tissue, an organ, etc.). The non-biological object may include a radioactive ore, an antique, etc. In the present disclosure, "object" and "subject" are used interchangeably. As shown in FIG. 1, the MR-PET apparatus 100 may include a shell 110, a magnet assembly 120, a PET detection device 130, a supporting component 140, an RF coil 150, and a signal shielding component 170.

The shell 110 may be configured to protect one or more components (e.g., the magnet assembly 120, the PET detection device 130, the supporting component 140, the RF coil 150, the signal shielding component 170) of the MR-PET apparatus 100.

The magnet assembly 120 may configured to generate a static main magnetic field in the detection region 160. The magnet assembly 120 may be of various types including, for example, a permanent magnet, a superconducting electromagnet, a resistive electromagnet, etc. The magnet assembly 120 may have any magnetic field intensity, for example, 0.2 Tesla, 0.5 Tesla, 1.0 Tesla, 1.5 Tesla, and 3.0 Tesla.

A gradient magnet may generate magnetic field gradients to the main magnetic field in the X, Y, and/or Z directions (or axes). In some embodiments, the gradient magnet may include an X-direction (or axis) coil, a Y-direction (or axis) coil, a Z-direction (or axis) coil, etc. For example, the Z-direction coil may be designed based on a circular (Maxwell) coil configuration, while the X-direction coil and the Y-direction coil may be designed based on the saddle (Golay) coil configuration. In some embodiments, the gradient magnet may form part of the magnet assembly 120. Alternatively, the gradient magnet may be independent of the magnet assembly 120.

The PET detection device 130 may be configured to detect signals, for example, attenuated radioactive rays, radiation events, etc. For example, the signals may be gamma photons emitted by the object. In particular, a radioactive tracer (e.g., fluorine-18) may be introduced into the object to be scanned. The radioactive tracer may decay and emit positrons. The positrons may encounter with electrons of the object and produce a pair of annihilation photons (e.g., gamma photons). Merely by way of example, the crystals of the PET detection device 130 may generate an optical signal in response to the detected signals. The optical signal may be converted to an electric signal by a photoelectric converter. A PET image may be generated based on the electric signal.

In some embodiments, the PET detection device 130 may include a plurality of detection units (e.g., detection units 230 as illustrated in FIG. 2). The plurality of detection units may be arranged around the supporting component 140. The arrangement of the plurality of detection units may correspond to the shape of the supporting component 140. For example, the supporting component 140 may have a ring shape and the detection units may be uniformly arranged around the outer surface of the supporting component 140 as a detection ring (as shown in FIG. 1). Similarly, the detection units may be arranged along an arc, a rectangle, a triangle, or a curved array, etc. As used herein, the outer surface of the supporting component 140 may refer to a surface of the supporting component 140 that is away from the object being scanned.

The supporting component 140 may be configured to support one or more components of the MR-PET apparatus 100, such as the PET detection device 130. The supporting component 140 may be a cylindrical structure, as shown in FIG. 1. In some embodiments, the supporting component 140 may include a first section and a second section. The second section may have a lower attenuation rate of the photons (also referred to as photon rays or photon beams) than the first section. In some embodiments, the first section and the second section may be made of a same material. The thickness of the second section may be less than the thickness of the first section (e.g., the second section may include a groove). In some embodiments, an auxiliary supporting body may be connected to the second section. The strength of the auxiliary supporting body may be less than the strength of the first section and/or the second section. The auxiliary supporting body may have a lower attenuation rate of the photon rays than the first section and/or the second section. More descriptions of the supporting component 140 may be found elsewhere in the present disclosure (e.g., FIGS. 3, 4, 5, and descriptions thereof).

In some embodiments, the PET detection device 130 may be supported on the supporting component 140. For example, the PET detection device 130 may be positioned such that at least a portion of the plurality of photons penetrate through the second section of the supporting component 140 and reach the PET detection device 130 such that the attenuation of the photons may be small. More descriptions of the position of the PET detection device 130 may be found elsewhere in the present disclosure (e.g., FIG. 5 and descriptions thereof).

The RF coil 150 may emit radiofrequency (RF) pulses (or RF signals) to and/or receive RF signals from an object being scanned. As used herein, an RF pulse may include an excitation RF pulse and a refocusing RF pulse. The RF coil 150 may include a quotient difference (QD) orthogonal coil and/or a phase-array coil. In some embodiments, the RF coil 150 may include a plurality of different types of RF coils. The different types of RF coils 150 may be used for the scanning of different parts of the object. For example, the different types of RF coils 150 may include a head coil specialized for the scanning of the head of the object, a knee joint coil specialized for the scanning of a knee joint of the object, etc. The RF coil 150 may include a volume coil and/or a local coil. For example, the volume coil may include a dipole coil, a birdcage coil, a transverse electromagnetic coil, a loop coil, a surface coil, etc. The local coil may include a solenoid coil, a saddle coil, a flexible coil, etc.

In some embodiments, the RF coil 150 may include a plurality of coil units (e.g., a coil unit 220 as illustrated in FIG. 2). The plurality of coil units may be arranged around the supporting component 140 in a suitable configuration. For example, the plurality of coil units may be arranged around the inner surface of the supporting component 140. As used herein, the inner surface of the supporting component 140 may refer to a surface of the supporting component 140 that faces the object being scanned. In some embodiments, each coil unit may correspond to one or more of the detection units of the PET detection device 130. The number (or count) of the coil units may be the same as or different from the number (or count) of the detection units. For example, each coil unit (e.g., the coil unit 220) may correspond to a detection unit (e.g., the detection unit 230) of the PET detection device 130, as illustrated in FIG. 2. In other words, the plurality of coil units may be uniformly arranged around the inner surface of the supporting component 140 corresponding to the uniformly arranged detection units. Accordingly, the RF signal transmitted from the RF coil 150 to the object may be uniform, which may ensure a good quality of an RF signal and a good quality of an MR image of the object.

As another example, each coil unit may correspond to two or more detection units of the PET detection device 130 (as illustrated in FIG. 1). The plurality of coil units may be spaced apart from each other. In some embodiments, the plurality of coil sub-units may be uniformly arranged around the supporting component 140 about the Z direction (into/out of the page as illustrated in FIG. 1 or along the long axis of a gantry of the MR-PET apparatus 100). Accordingly, the RF signals emitted by the RF coil 150 may be transmitted to the object in multiple directions. Hence the performance of the RF coil 150 may be improved.

In some embodiments, the MR-PET apparatus 100 may further include a signal shielding component 170 placed between the PET detection device 130 and the RF coil 150. The signal shielding component 170 may be configured to shield the PET detection device 130 from at least part of RF signals generated by the RF coil 150. For example, as the RF signals emitted by the RF coil 150 are transmitted in multiple directions, at least part of the RF signal may be transmitted in a direction to the PET detection device 130. The signal shielding component 170 may shield or block the at least part of the RF signals from reaching the PET detection device. Alternatively or additionally, the signal shielding component 170 may reduce the strength of the at least part of the RF signals such that the strength of the RF signals that penetrate through the signal shielding component 170 does not harm or cause inference to the PET detection device 130. The signal shielding component 170 may eliminate or reduce an interference (e.g., a coupling) between the RF coil 150 and the PET detection device 130. For example, the signal shielding component 170 may protect the PET detection device 130 from RF signal interferences caused by the RF coil 150. As another example, the signal shielding component 170 may protect the RF coil 150 from PET signal interferences caused by the PET detection device 130 or the photons from the radiation events of the PET imaging.

Figure 7:
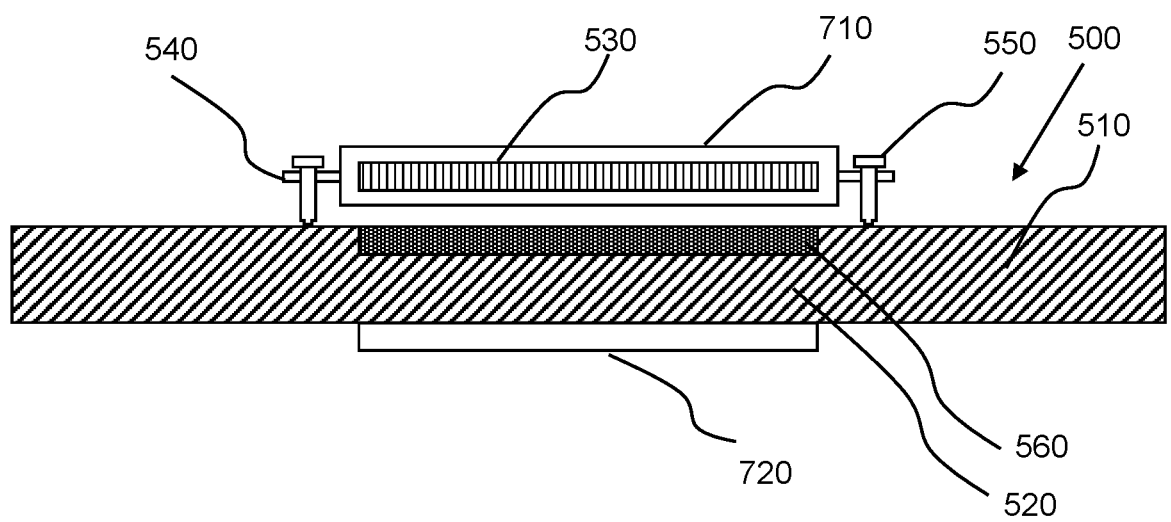
FIG. 7 is an axial sectional view of an exemplary MR-PET apparatus according to some embodiments of the present disclosure.

In some embodiments, the signal shielding component 170 may include one or more shielding layers attached to at least part of an external surface of the PET detection device 130. In some embodiments, the shielding layer may be attached to an inner surface of the PET detection device 130 that faces the RF coil 150. Alternatively or additionally, the shielding layer(s) may be attached to all external surfaces of the PET detection device 130 to ensure a good shielding effect between the RF coil 150 and the PET detection device 130 and high sensitivity of the PET detection device 130. For example, the PET detection device 130 may be a cuboid, and the shielding layers may be attached to all six surfaces of the PET detection device 130 (as shown in FIG. 7). In some embodiments, the shielding layers attached to different surfaces of the PET detection device 130 may be of different sizes, thicknesses, and/or shapes.

Figure 6:
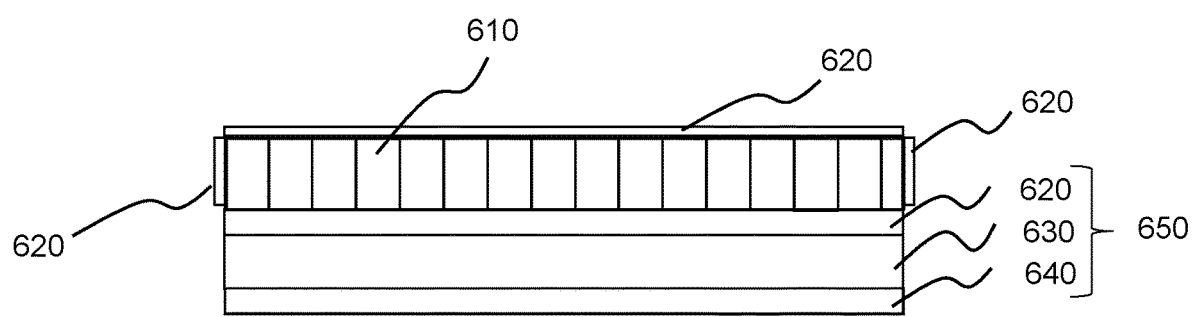
FIG. 6 is an axial view of an exemplary connection between a PET detection device and a connection board according to some embodiments of the present disclosure.
Figure 8:
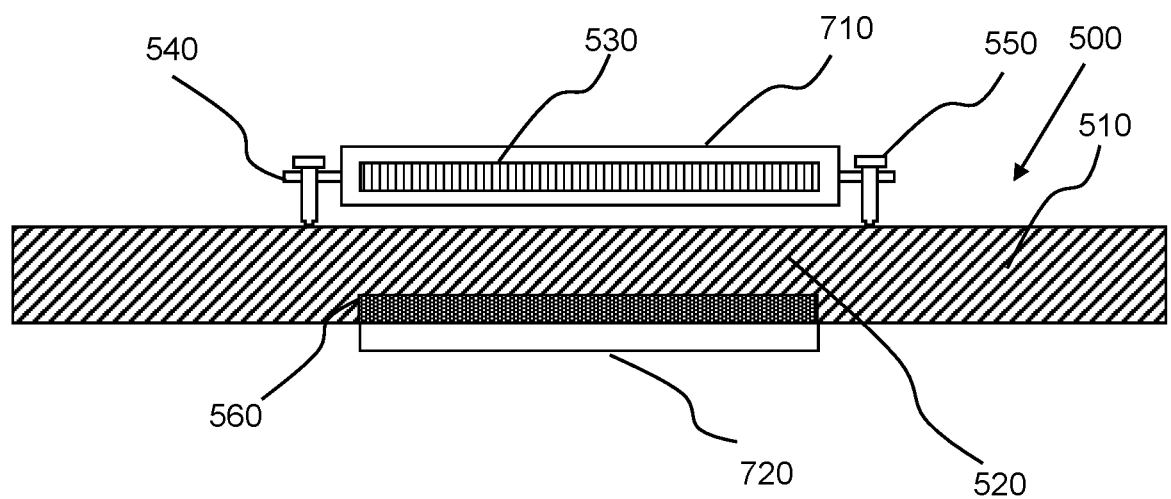
FIG. 8 is an axial sectional view of an exemplary MR-PET apparatus according to some embodiments of the present disclosure.
Figure 9:
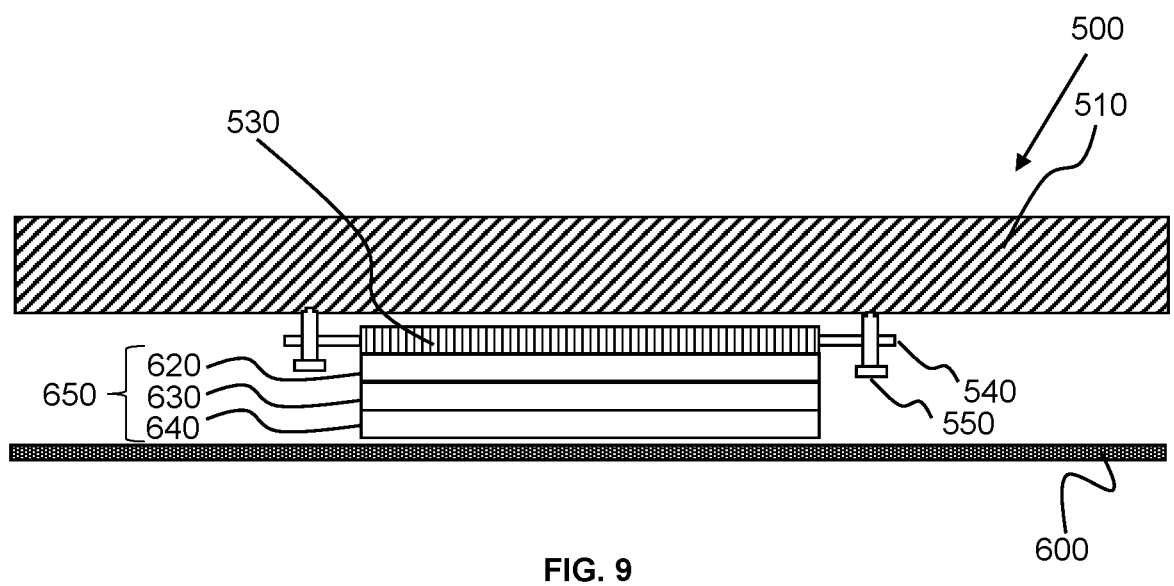
FIG. 9 is an axial sectional view of an exemplary MR-PET apparatus according to some embodiments of the present disclosure.

In some embodiments, the shielding layer may include a first side and a second side. As used herein, the first side may refer to a side that faces the object, and the second side may refer to a side that is away from the object, or vice versa. The first side of the shielding layer may be attached to the RF coil 150 and the second side of the shielding layer may be attached to the PET detection device 130 (as illustrated in FIG. 6 and FIG. 9). In some embodiments, the first side of the shielding layer may be attached to the RF coil 150 and the second side of the shielding layer may be attached to the supporting component 140 (as illustrated in FIG. 8). More descriptions of the position of the signal shielding component 170 may be found elsewhere in the present disclosure (e.g., FIGS. 6-9, and descriptions thereof).

The signal shielding component 170 may be made of at least one electrically conductive material. Suitable electrically conductive materials may include a metal, a metal oxide, an alloy, rubber, graphite, a semiconductor, a composite polymer, or the like, or any combination thereof. The signal shielding component 170 may have any suitable two-dimensional (2D) or three-dimensional (3D) configuration. For example, the signal shielding component 170 may have the configuration of a film, a mesh, or the like, or any combination thereof. In some embodiments, the signal shielding component 170 may be a metal film (e.g., a copper film), a metal plate, a sprayed metal layer or coating, or the like. As another example, the signal shielding component 170 may be a metal mesh.

In some embodiments, the signal shielding component 170 (e.g., a conductive metal film) may be attached to the PET detection device 130 and/or the supporting component 140 by any suitable technique, e.g., spin coating, dip coating, screen printing, transfer coating, sputtering, physical vapor deposition, chemical vapor deposition, or the like, or any combination thereof. In some embodiments, the signal shielding component (e.g., a metal mesh) may be assembled onto the PET detection device 130 and/or the supporting component 140 via an adhesive. In some embodiments, the MR-PET apparatus 100 may further include an electrical insulation component (not shown in FIG. 1) placed between the RF coil 150 and the signal shielding component 170.

In some embodiments, at least one of the signal shielding component 170, the insulation component, and the RF coil 150 may be integrated on a same circuit board (e.g., a printed circuit board (PCB)). The integrated circuit board (also referred to as a connection board) may be mechanically attached to the inner surface of the PET detection device 130. More descriptions of the connection board may be found elsewhere in the present disclosure (e.g., FIG. 6, and descriptions thereof).

The connection board described in the present disclosure may integrate the PET detection device 130 with the RF coil 150. Accordingly, a supporting structure for the RF coil 150 may be omitted, which may make full use of the space in the MR-PET apparatus 100. The space for accommodating the PET detection device 130, the signal shielding component, and the RF coil 150 may be reduced, thereby avoiding an excessive size of other components (e.g., the magnet assembly 120) of the MR-PET apparatus 100. Accordingly, the cost may be saved. The scanning space in the MR-PET apparatus 100 for housing a patient is not reduced due to the integration of the PET detection device 130 and the MR imaging device, thereby making the patient feel more comfortable during a scanning process. In addition, the attenuation of the gamma photons reaching the PET detection device 130 may also be alleviated due to the omission of a support structure of the RF coil 150, thereby improving the sensitivity of the PET detection device 130.

In some embodiments, the MR-PET apparatus 100 may further include a gantry (not shown in FIG. 1), configured to support one or more components of the MR-PET apparatus 100, (e.g., the shell 110, the magnet assembly 120, the PET detection device 130, the supporting component 140, the RF coil 150, the signal shielding component 170). In some embodiments, the inner surface of the gantry may form a detection region 160 (or referred to as a detection channel, scanning channel, or scanning space). The object to be scanned may be placed on a scanning table (not shown in FIG. 1) and moved along the Z-direction to a desired position in the detection region 160 and be scanned (e.g., undergoing an MR scan and/or a PET scan).

It should be noted that the MR-PET apparatus 100 shown in FIG. 1 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 3:
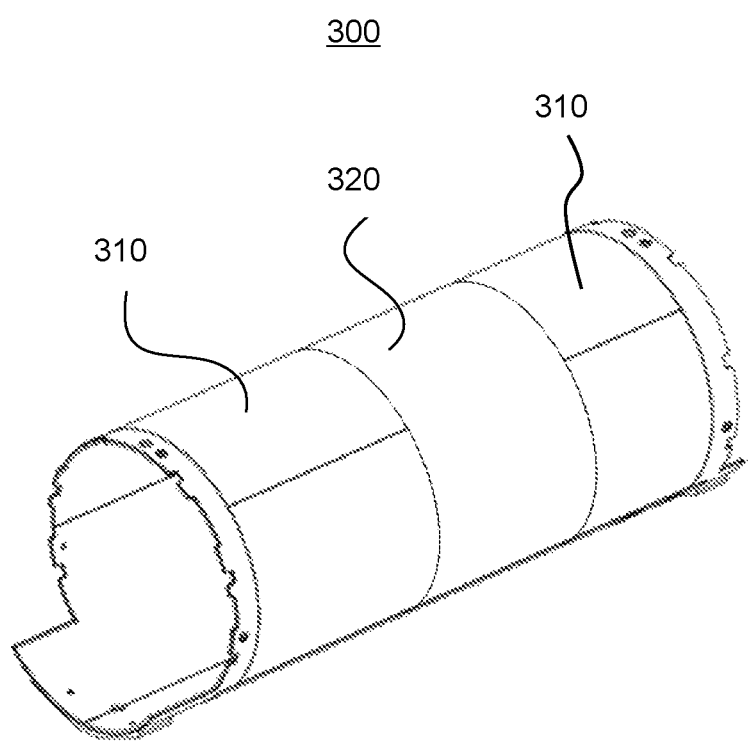
FIG. 3 is a perspective view of an exemplary supporting component according to some embodiments of the present disclosure.
Figure 4:
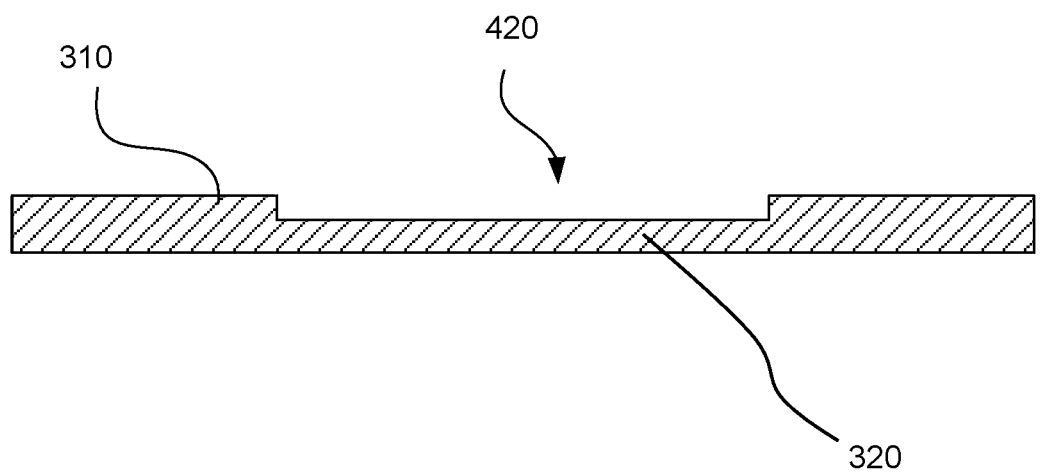
FIG. 4 is an axial sectional view of a part of an exemplary supporting component according to some embodiments of the present disclosure.

FIG. 3 is a perspective view of an exemplary supporting component according to some embodiments of the present disclosure. FIG. 4 is an axial sectional view of a part of an exemplary supporting component according to some embodiments of the present disclosure. In some embodiments, the supporting component 300 may correspond to the supporting component 140 or a portion thereof. As shown in FIG. 3, the supporting component 300 may include at least one first section 310 (e.g., two first sections 310 as shown in FIG. 3) and a second section 320.

In some embodiments, the first section 310 and the second section 320 may be made of a same material or different materials. As shown in FIG. 4, the thickness of the first section 310 may be greater than the thickness of the second section 320. For example, the second section 320 may be formed by making a groove or indentation (e.g., a groove 420) on the supporting component 300. The groove (or indentation) may be formed on the outer surface (e.g., a surface away from the object during use) and/or the inner surface (e.g., a surface facing the object during use) of the supporting component 300. As the thickness of the second section 320 is less than the thickness of the first section 310, the second section 320 may have a lower attenuation rate of the photons than the first section 310. In other words, signals detected by the PET detection device (e.g., the PET detection device 130) resulting from the photons that penetrate through the second section 320 may be more accurate than the signals resulting from the photons that penetrate through the first section 310.

Figure 5:
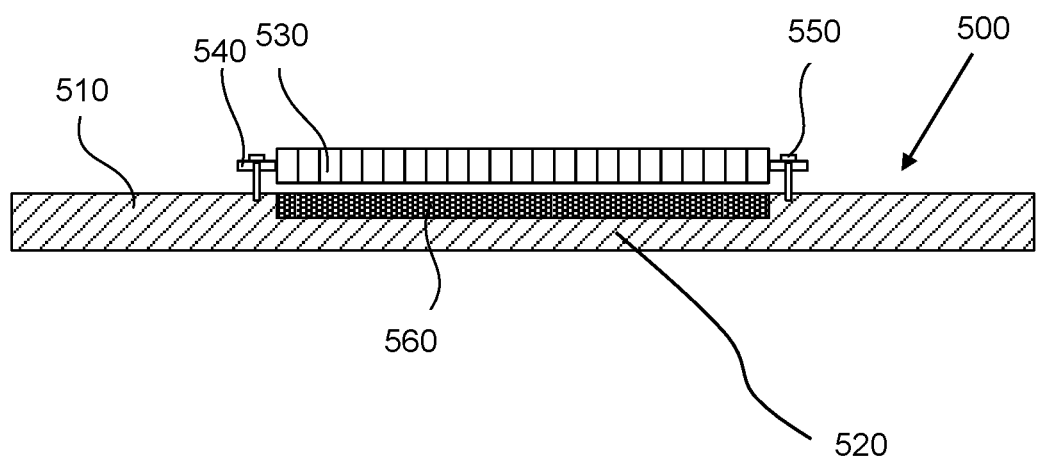
FIG. 5 is an axial sectional view of an exemplary connection between a PET detection device and a supporting component according to some embodiments of the present disclosure.

In some embodiments, an auxiliary supporting body (e.g., the auxiliary supporting body 560) may be placed in the groove (or indentation) of the second section 320 of the supporting component 300 (as shown in FIG. 5). The width of the second section 320 may be greater than or equal to the width of the auxiliary supporting body. The thickness of the auxiliary supporting body may be (roughly) the same as the difference between the thickness of the first section 310 and the thickness of the second section 320, or the depth of the groove (or indentation) where the auxiliary supporting body is located on the supporting component 300.

The first section 310 and/or the second section may be made of any suitable material that has high strength and/or stability to provide a stable support for the PET detection device (e.g., the PET detection device 130). For example, the first section 310 and/or the second section 320 may be made of, for example, glass fiber, carbon fiber, etc. The auxiliary supporting body may be made of any suitable material that has lower structural strength and/or a lower attenuation rate of photons than the first section 310 and/or the second section 320. For example, the auxiliary supporting body may be made of a foam material, a honeycomb material, etc.

It should be noted that the supporting component shown in FIGS. 3 and 4 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 5 is an axial sectional view of an exemplary connection between a PET detection device and a supporting component according to some embodiments of the present disclosure. In some embodiments, the supporting component 500 may correspond to the supporting component 140, the supporting component 300, or a portion thereof. The PET detection device may correspond to the PET detection device 130, or a portion thereof. The supporting component 500 may correspond to the supporting component 140, the supporting component 300, or a portion thereof.

As shown in FIG. 5, the supporting component 500 may include a first section 510 and a second section 520. The second section 520 may be formed by making a groove (or indentation) on the outer surface (e.g., the surface away from the object during use) of the supporting component 500. An auxiliary supporting body 560 may be placed in the groove (or indentation) of the second section 520 of the supporting component 500. The width of the auxiliary supporting body may be (roughly) equal to the width of the second section 520 (or the groove or indentation).

In some embodiments, a PET detection device 530 may be positioned such that at least a portion of the plurality of photons may penetrate through the second section 520 and reach the PET detection device 530. In some embodiments, the width of the PET detection device 530 may be less than or equal to the width of the second section 520, which may ensure that most or all of the photons reaching the PET detection device 530 penetrate through the second section 520.

In some embodiments, the auxiliary supporting body 560 may be mechanically attached to the second section 520 in any suitable manner to prevent the auxiliary supporting body from being inadvertently or unintentionally detached from the second section 520. For example, the auxiliary supporting body 560 may be mechanically attached to the second section 520 using a chemical (e.g., an adhesive), a mechanical component (e.g., a nail, a screw, a nut), or the like, or any combination thereof. In some embodiments, the auxiliary supporting body 560 may be adhesively attached to the second section 520 of the supporting component 500, which may provide a stable and reliable connection between the auxiliary supporting body and the second section 520. In some embodiments, even though the auxiliary supporting body 560 is made of a material with relatively low strength, the tight attachment of the auxiliary supporting body 560 to the groove (or indentation) of the second section 520 may provide a good overall strength of the supporting component 500 (e.g., against torques or bends) without significantly increasing the attenuation rate of photons. Compared with a supporting component of which the first section and the second section are of the same thickness and without the auxiliary supporting body 560, the strength of the supporting component 500 may be slightly less, but, the attenuation rate of photons of the supporting component 500 may be significantly lower.

The PET detection device 530 may be mounted on the supporting component 500 in any suitable manner. For example, the PET detection device 530 may include one or more mounting devices 540. The mounting device 540 may be configured to facilitate the installation of the PET detection device 530 on the supporting component 500. Merely by way of example, the mounting devices 540 may include mounting boards with through holes. The mounting devices 540 may be mounted on both ends of the PET detection device 530. One or more screws 550 may be screwed into the through holes of the mounting device 540 and mount the PET detection device 530 on the supporting component 500.

It should be noted that the connection between the PET detection device and the supporting component shown in FIG. 5 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the auxiliary supporting body 560 may have any shape and size. In some embodiments, the PET detection device 530 may be mounted on the supporting component 500 using a mechanical component (e.g., a nail), or a chemical (e.g., an adhesive), or the like, or any combination thereof.

FIG. 6 is an axial view of an exemplary connection between a PET detection device and a connection board according to some embodiments of the present disclosure. The PET detection device 610 may correspond to the PET detection device 130, the PET detection device 530, or a portion thereof.

As shown in FIG. 6, the connection board 650 may have a multi-layer structure. In some embodiments, the connection board 650 may be a circuit board (e.g., a printed circuit board (PCB)). The manufacturing of the connection board 650 in the form of a PCB may be convenient. In some embodiments, the connection board 650 may include a signal shielding component 620, an insulation component 630, and an RF coil 640. The signal shielding component 620 may correspond to signal shielding component 170, or a portion thereof. The RF coil 640 may correspond to the RF coil 150, or a portion thereof.

The signal shielding component 620 may be mechanically attached to one or more external surfaces of the PET detection device 610. As used herein, a first component being mechanically attached or connected to a second component indicates that the second component provides a mechanical support to the first component. In some embodiments, the signal shielding component 620 may include one or more shielding layers (e.g., metal layers). The shielding layer may include a first side and a second side. The first side of the shielding layer may be mechanically attached to the insulation component 630 and the second side of the shielding layer may be mechanically attached to the PET detection device 610. In some embodiments, the one or more shielding layers may be of same or different size(s), shape(s), and/or thickness(es). For example, the shielding layer between the PET detection device 610 and the RF coil 640 may be thin while the shielding layer attached to the side surfaces or the top surface of the PET detection device 610 may be thick. In some embodiments, the RF coil 640 may be grounded via the signal shielding component 620. In other words, the signal shielding component 620 may be grounded for the RF coil 640, which may guarantee the operation safety of the RF coil 640. The insulation component 630 placed between the RF coil 640 and the signal shielding component 620 may be configured to electrically insulate the RF coil 640 from the signal shielding component 620.

In some embodiments, the RF coil 640 may include a first number (or count) of coil units. The PET detection device 610 may include a second number (or count) of detection units. The first number (or count) may be the same as or different from the second number (or count). The signal shielding component 620 may include a third number (or count) of shielding units. The third number (or count) may be the same as or be different from the first number (or count) and/or the second number (or count). In some embodiments, a coil unit may be paired with a shielding unit. A pair of a coil unit and a shielding unit may be installed on a connection board unit. The connection board 650 may include a plurality of connection board units. A connection board unit may be mechanically attached to one of the detection units. In some embodiments, the shape and/or size of the connection board unit may be the same as or different from the shape and/or size of the corresponding detection unit.

It should be noted that the connection between a PET detection device and a connection board shown in FIG. 6 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the insulation component 630 may be omitted.

FIG. 7 is an axial sectional view of an exemplary MR-PET apparatus according to some embodiments of the present disclosure. In some embodiments, the MR-PET apparatus 700 may be an exemplary embodiment of the MR-PET apparatus 100 or a portion thereof.

As shown in FIG. 7, a supporting component 500 may include a first section 510 and a second section 520. The thickness of the second section 520 may be less than the thickness of the first section 510. For example, the second section 520 may be formed by making a groove or indentation (e.g., a groove 420) on the outer surface of the supporting component 500. An auxiliary supporting body 560 may be placed in the groove or indentation of the second section 520 of the supporting component 500. A PET detection device 530 may be mechanically attached on the outer surface of the supporting component 500 via one or more mounting devices 540 and one or more screws 550. The width of the PET detection device 530 may be less than or equal to the width of the second section 520. A signal shielding component 710 may include a shielding layer attached to all external surfaces of the PET detection device 530. An RF coil 720 may be attached to the inner surface of the supporting component 500.

During a scanning of an object, a plurality of photons may be emitted from the object. At least part of the plurality of photons may be transmitted in a direction towards the PET detection device 530. The signal shielding component 710 may shield or block the at least part of the RF signals generated by the RF coil 720 from reaching the PET detection device 530. Alternatively or additionally, the signal shielding component 710 may reduce the strength of the at least part of the RF signals such that the strength of the RF signal that penetrate through the signal shielding component 710 does not harm or cause inference to the PET detection device 530. For example, the second section 520 and the auxiliary supporting body 560 may have a lower attenuation rate of the photons than the first section 510. Accordingly, the one or more photons may reach the PET detection device 530 with low attenuation. In some embodiments, the supporting component 500 may be made of insulating materials and act as an insulation component as described elsewhere in the present disclosure.

FIG. 8 is an axial sectional view of an exemplary MR-PET apparatus according to some embodiments of the present disclosure. In some embodiments, the MR-PET apparatus 800 may be an exemplary embodiment of the MR-PET apparatus 100 or a portion of the MR-PET apparatus 100. The MR-PET apparatus 800 may be similar to the MR-PET apparatus 700 except the second section 520 and the auxiliary supporting body 560 with a lower attenuation rate of the photons are placed away from the PET detection device 530 and closed to the RF coil 720. As shown in FIG. 8, the auxiliary supporting body 560 may be mechanically attached to the RF coil 720.

The operations of the MR-PET apparatus 800 during a scanning of the object, may be similar to the operations of the MR-PET apparatus 700 and are not repeated herein.

FIG. 9 is an axial sectional view of an exemplary MR-PET apparatus according to some embodiments of the present disclosure. In some embodiments, the MR-PET apparatus 900 may be an exemplary embodiment of the MR-PET apparatus 100 or a portion of the MR-PET apparatus 100. As shown in FIG. 9, the MR-PET apparatus 900 may include the connection board 650 (e.g., a circuit board, a PCB) attached to a side of the PET detection device 530 close to the object. The connection board 650 may include the signal shielding component 620, the insulation component 630, and the RF coil 640 as described elsewhere in the present disclosure (e.g., FIG. 6, and descriptions thereof). The width of the connection board 650 may be the same as or different from the width of the PET detection device 530. The width of the connection board 650 may be less than the width of the supporting component 500. The supporting component 500 may include a first section 510. The PET detection device 530 may be mechanically attached to the inner surface of the supporting component 500 via one or more mounting devices 540 and one or more screws 550. The MR-PET apparatus 900 may further include an inner plate 600 placed away from the supporting component 500 (e.g., the inner plate 600 is on a side of the supporting component 500 that is close to the object). The inner plate 600 may form a patient bore (e.g., the detection region 160), and the thickness of the inner plate 600 may be less than the thickness of the supporting component 500.

Figure 10:
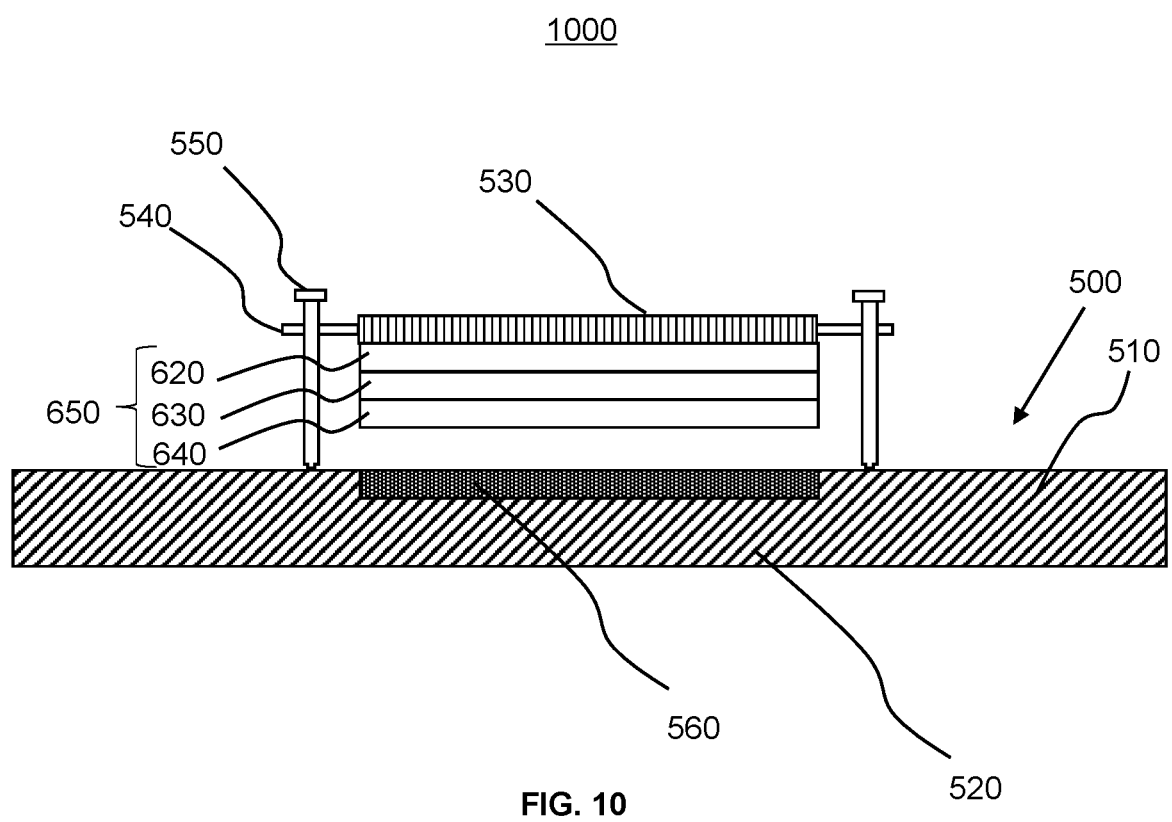
FIG. 10 is an axial sectional view of an exemplary MR-PET apparatus according to some embodiments of the present disclosure.

FIG. 10 is an axial sectional view of an exemplary MR-PET apparatus according to some embodiments of the present disclosure. In some embodiments, the MR-PET apparatus 1000 may be an exemplary embodiment of the MR-PET apparatus 100 or a portion of the MR-PET apparatus 100. The MR-PET apparatus 1000 may be similar to the MR-PET apparatus 800 except the connection board 650 is placed on a side of the supporting component 500 away from the object. As shown in FIG. 10, the connection board 650 may be attached to the surface of PET detection device 530. The shape and/or size of the connection board 650 may be the same as that of the PET detection device 530.

During a scanning of an object, a plurality of photons may be emitted from the object. At least part of the plurality of photons may be transmitted in a direction towards the PET detection device 530. The signal shielding component 620 may shield or block the at least part of the RF signals generated by the RF coil 640 from reaching the PET detection device 530. Alternatively or additionally, the signal shielding component 620 may reduce the strength of the at least part of the RF signals such that the strength of the RF signals that penetrates through the signal shielding component 620 does not harm or cause inference to the PET detection device 530. Since the RF signals penetrate through the second section 520 of the supporting component 500 when the RF signals are transmitted to the object or emitted from the object. The second section 520 may be made of a material that can be easily penetrated through by the RF signals such that the RF signals is not blocked by the second section 520 of the supporting component 500.

Figure 11:
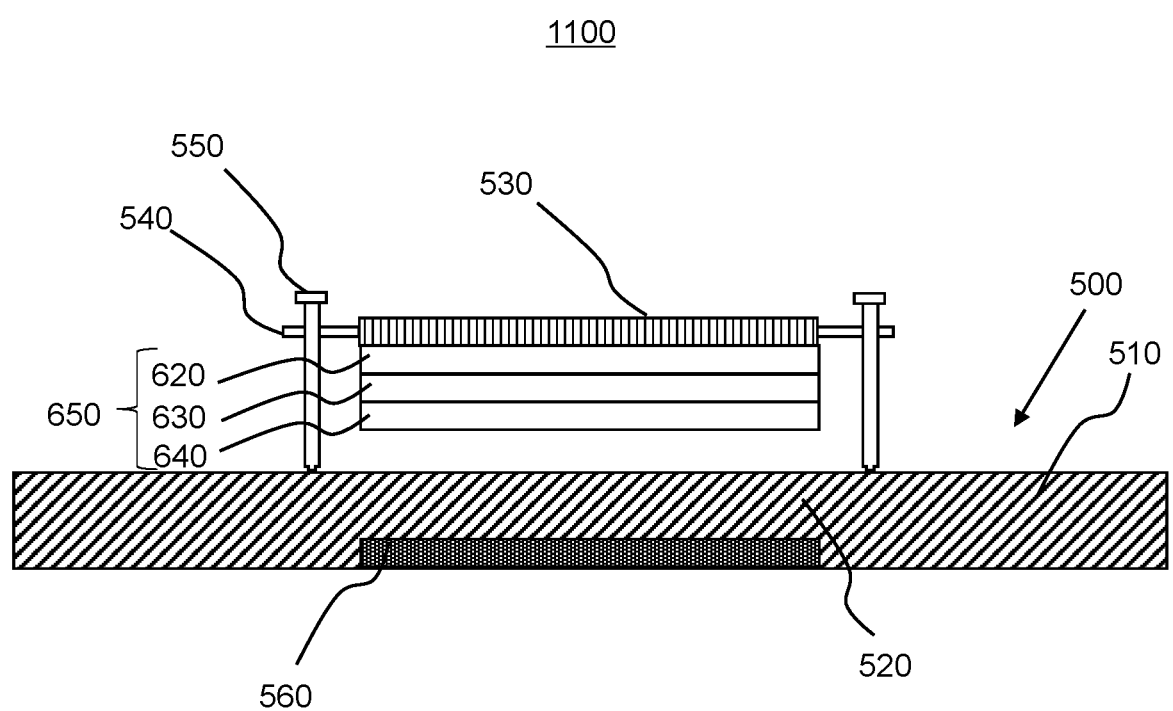
FIG. 11 is an axial sectional view of an exemplary MR-PET apparatus according to some embodiments of the present disclosure.

FIG. 11 is an axial sectional view of an exemplary MR-PET apparatus according to some embodiments of the present disclosure. In some embodiments, the MR-PET apparatus 1100 may be an exemplary embodiment of the MR-PET apparatus 100 or a portion of the MR-PET apparatus 100. The MR-PET apparatus 1100 may be similar to the MR-PET apparatus 1000 except that the second section 520 and the auxiliary supporting body 560 with a lower attenuation rate of the photons may be placed away from the connection board 650.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A magnetic resonance (MR)-positron emission tomography (PET) apparatus, comprising:
   a supporting component;
   a PET detection device supported on the supporting component, the PET detection device being configured to receive a plurality of photons;
   a radio frequency (RF) coil, configured to generate or receive an RF signal, wherein the RF coil includes a plurality of coil units arranged around the supporting component, and the plurality of coil units are spaced apart from each other; and
   a signal shielding component placed between the PET detection device and the RF coil, the signal shielding component being configured to shield the PET detection device from at least part of the RF signal; and
   an insulation component, wherein
      the RF coil, the insulation component, and the signal shielding component are integrated on a connection board,
      a first side of the insulation component is mechanically attached to the RF coil,
      a second side of the insulation component is mechanically attached to the signal shielding component,
      the insulation component is configured to electrically insulate the RF coil from the signal shielding component,
      the signal shielding component is mechanically attached to the PET detection device;
      the connection board is placed on an outer side of the supporting component; and
      a width of the connection board along an axial direction of the supporting component is less than or equal to a width of the PET detection device.

2. The MR-PET apparatus of claim 1, wherein the supporting component includes a first section and a second section, wherein
   the second section has a lower attenuation rate of the photons than the first section, and
   the PET detection device is positioned such that at least a portion of the plurality of photons penetrate through the second section and reach the PET detection device.

3. The MR-PET apparatus of claim 2, wherein the supporting component including the first section and the second section is an integral body and the second section is thinner than the first section.

4. The MR-PET apparatus of claim 3, wherein the first section and the second section are made of carbon fiber or glass fiber.

5. The MR-PET apparatus of claim 2, wherein the supporting component further includes an auxiliary supporting body mechanically attached to the second section.

6. The MR-PET apparatus of claim 5, wherein the auxiliary supporting body is made of a foam material or a honeycomb material.

7. The MR-PET apparatus of claim 5, wherein the auxiliary supporting body has a lower attenuation rate of photons than the first section and the second section.

8. The MR-PET apparatus of claim 1, wherein the signal shielding component is made of one or more electrically conductive materials.

9. The MR-PET apparatus of claim 1, wherein the signal shielding component includes a shielding layer mechanically attached to at least part of an external surface of the PET detection device.

10. The MR-PET apparatus of claim 1, wherein the RF coil includes a first count of coil units, the PET detection device includes a second count of detection units, and the first count is the same as the second count.

11. The MR-PET apparatus of claim 10, wherein the connection board includes a plurality of connection board units, the signal shielding component includes a third count of shielding units, and the third count is the same as the first count or the second count, and wherein
   each of the coil units are paired with one of the shielding units, each pair of a coil unit and a shielding unit are installed on a connection board unit of the plurality of connection board units, and each connection board unit of the plurality of connection board units is mechanically attached to one of the detection unit.

12. The MR-PET apparatus of claim 1, wherein the connection board is a circuit board.

13. The MR-PET apparatus of claim 1, wherein the PET detection device includes a plurality of detection units, the plurality of detection units being arranged in a ring shape.

14. The MR-PET apparatus of claim 1, wherein the RF coil includes at least one of a dipole coil, a birdcage coil, a transverse electromagnetic coil, a loop coil, or a surface coil.

15. The MR-PET apparatus of claim 1, wherein the signal shielding component has a configuration of a film or a mesh.

16. The MR-PET apparatus of claim 1, further comprising:

a gantry, configured to hold at least one of the supporting component, the PET detection device, the RF coil, or the signal shielding component, wherein an inner surface of the gantry forms a detection region, and the detection region is configured to accommodate an object.

17. The MR-PET apparatus of claim 1, further comprising:

a main magnet, configured to generate a main magnetic field; and a gradient magnet, configured to generate magnetic field gradients.

* * * * *